(12) United States Patent
Isono et al.

(10) Patent No.: US 9,879,124 B2
(45) Date of Patent: Jan. 30, 2018

(54) METHOD FOR MANUFACTURING WATER-INSOLUBLE MOLDED ARTICLE AND WATER-INSOLUBLE MOLDED ARTICLE

(71) Applicant: DAINICHISEIKA COLOR & CHEMICALS MFG. CO., LTD., Tokyo (JP)

(72) Inventors: Yasuyuki Isono, Tokyo (JP); Yasuharu Noishiki, Yokohama (JP)

(73) Assignee: DAINICHISEIKA COLOR & CHEMICALS MFG. CO., LTD., Tokyo (JP)

( * ) Notice: Subject to any disclaimer, the term of this patent is extended or adjusted under 35 U.S.C. 154(b) by 0 days.

(21) Appl. No.: 14/910,930

(22) PCT Filed: Aug. 22, 2014

(86) PCT No.: PCT/JP2014/071988
§ 371 (c)(1),
(2) Date: Feb. 8, 2016

(87) PCT Pub. No.: WO2015/029892
PCT Pub. Date: Mar. 5, 2015

(65) Prior Publication Data
US 2016/0208064 A1    Jul. 21, 2016

(30) Foreign Application Priority Data

Aug. 29, 2013   (JP) .................. 2013-177746

(51) Int. Cl.
| | | |
|---|---|---|
| C08J 7/14 | (2006.01) | |
| A61K 47/36 | (2006.01) | |
| C08J 5/18 | (2006.01) | |
| A61L 27/20 | (2006.01) | |
| A61L 27/54 | (2006.01) | |
| A61L 31/04 | (2006.01) | |
| A61L 31/16 | (2006.01) | |
| A61L 27/50 | (2006.01) | |
| C08L 5/08 | (2006.01) | |
| C08L 5/04 | (2006.01) | |
| C08L 5/06 | (2006.01) | |
| C08L 5/10 | (2006.01) | |
| A61K 8/73 | (2006.01) | |

(52) U.S. Cl.
CPC .............. *C08J 7/14* (2013.01); *A61K 47/36* (2013.01); *A61L 27/20* (2013.01); *A61L 27/50* (2013.01); *A61L 27/54* (2013.01); *A61L 31/042* (2013.01); *A61L 31/16* (2013.01); *C08J 5/18* (2013.01); *A61K 8/733* (2013.01); *A61K 8/735* (2013.01); *A61K 8/736* (2013.01); *A61L 2300/602* (2013.01); *C08J 2301/26* (2013.01); *C08J 2305/04* (2013.01); *C08J 2305/06* (2013.01); *C08J 2305/08* (2013.01); *C08J 2305/10* (2013.01); *C08L 5/04* (2013.01); *C08L 5/06* (2013.01); *C08L 5/08* (2013.01); *C08L 5/10* (2013.01)

(58) Field of Classification Search
CPC ....................................................... C08J 7/14
See application file for complete search history.

(56) References Cited

U.S. PATENT DOCUMENTS

2012/0283213 A1* 11/2012 Tommeraas ............. A61K 8/11
514/54

FOREIGN PATENT DOCUMENTS

| EP | 0718312 | 6/1996 |
|---|---|---|
| EP | 1005874 | 6/2000 |
| EP | 1849472 | 10/2007 |
| EP | 2740499 | 6/2014 |
| JP | 6390507 | 4/1988 |
| JP | 0558881 | 3/1993 |
| JP | 05124968 | 5/1993 |
| JP | 06128395 | 5/1994 |
| JP | 0853501 | 2/1996 |
| JP | 2000044603 | 2/2000 |
| JP | 2000-191802 | 7/2000 |
| JP | 2002348243 | 12/2002 |
| JP | 2003518167 | 6/2003 |
| JP | 2003252905 | 9/2003 |
| JP | 2008013510 | 1/2008 |
| WO | 2006030965 | 3/2006 |

(Continued)

OTHER PUBLICATIONS

International Search Report issued in the corresponding International Application No. PCT/JP2014/071988, dated Nov. 11, 2014, 5 pages.

(Continued)

*Primary Examiner* — Theodore R. West
(74) *Attorney, Agent, or Firm* — Hamre, Schumann, Mueller & Larson, P.C.

(57) ABSTRACT

A process for producing a water-insoluble shaped material, including a step of treating a raw material shaped material containing a water-soluble salt of a polyanionic polysaccharide with a treatment liquid containing an acid anhydride to insolubilize the raw material shaped material in water, and the process makes it possible to simply produce a water-insoluble shaped material in which intrinsic characteristics of the polyanionic polysaccharide being a raw material are retained, which has a high safety in that a chemical cross-linking agent is not required, and which is useful as a medical material, a food material, a cosmetic material, and the like.

7 Claims, 2 Drawing Sheets

(56) References Cited

FOREIGN PATENT DOCUMENTS

| | | |
|---|---|---|
| WO | 2006080398 | 8/2006 |
| WO | 2013018759 | 2/2013 |

OTHER PUBLICATIONS

Extended European Search Report, issued in the corresponding European patent application No. 14840937.8, dated Mar. 20, 2017, 12 pages.

* cited by examiner

[Figure 1]
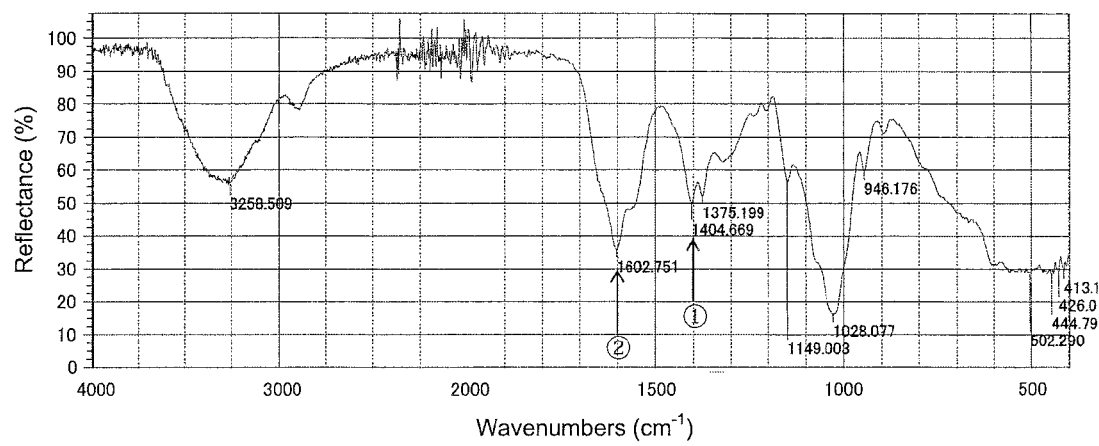
[Figure 2]
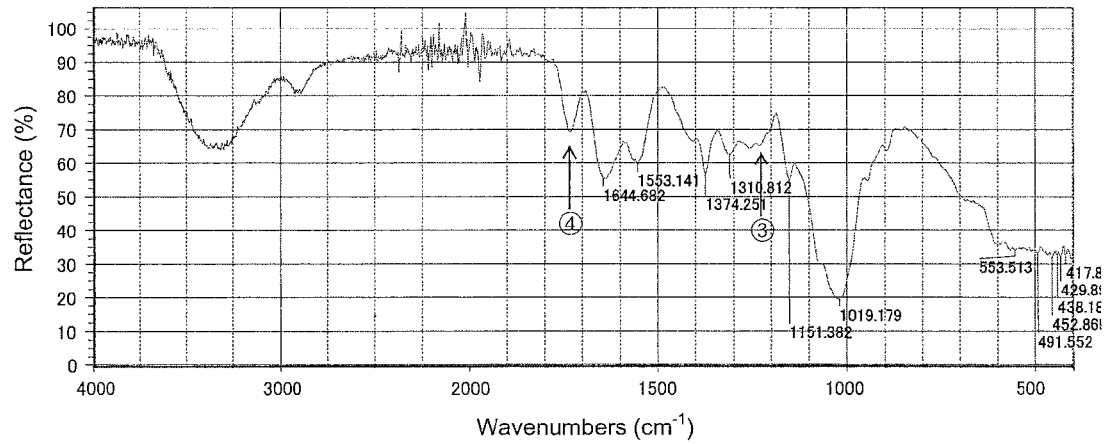

[Figure 3]
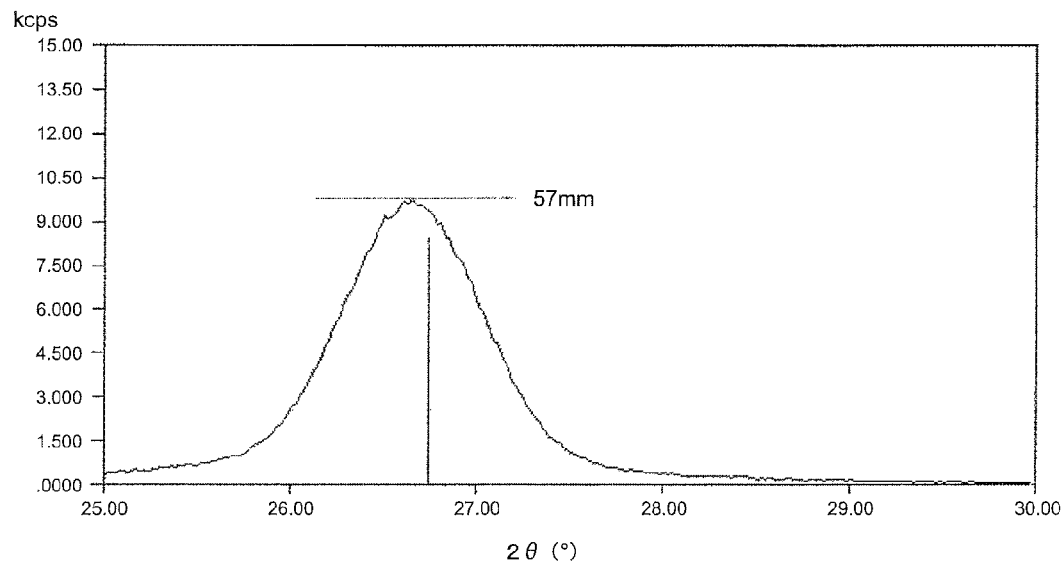
[Figure 4]
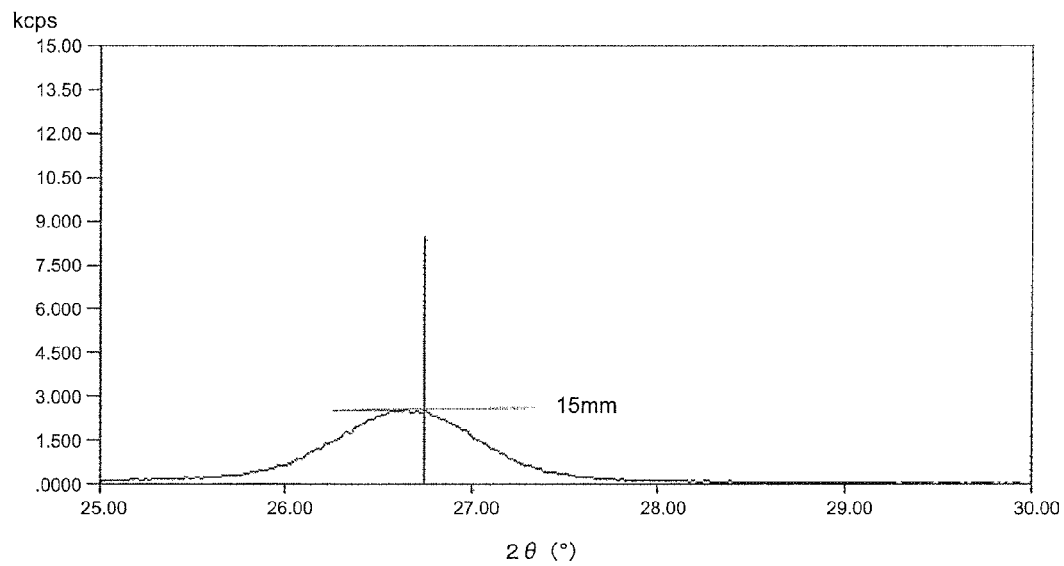

METHOD FOR MANUFACTURING WATER-INSOLUBLE MOLDED ARTICLE AND WATER-INSOLUBLE MOLDED ARTICLE

TECHNICAL FIELD

The present invention relates to a process for producing a water-insoluble shaped material, and also relates to a water-insoluble shaped material, an adhesion inhibitor, an injection material, and a sustained release preparation.

BACKGROUND ART

It is known that polyanionic polysaccharides such as hyaluronic acid and alginic acid exhibit moderate viscosity, adhesiveness, moisture-retaining properties, and biocompatibility. These polyanionic polysaccharides and salts thereof are therefore widely used as a raw material for medical materials, food materials, cosmetic materials, and the like.

Among others, hyaluronic acid has excellent characteristic properties such as moisture-retaining properties, also has high safety and biocompatibility, and therefore is utilized for various applications such as foods, cosmetics, and pharmaceuticals. In a medical field for example, hyaluronic acid is utilized for a raw material or the like of lubricants for joints, adhesion inhibitors, etc. However, sodium hyaluronate being a raw material has a high water-solubility, and thus insolubilizing treatment of some sort has to be applied to sodium hyaluronate depending on the application.

Various studies have so far been conducted on the process for insolubilizing sodium hyaluronate in water through crosslinking reaction that makes use of a carboxy group. In Patent Literature 1 for example, a process for producing a water-insoluble derivative of a polyanionic polysaccharide such as hyaluronic acid and carboxymethylcellulose through crosslinking reaction using a carbodiimide is described.

Moreover, in Patent Literatures 2 and 3, a process for insolubilizing in water a polyanionic polysaccharide such as hyaluronic acid and a carboxyalkylcellulose by forming ionic bonds using a polyvalent cation is described. Further, in Patent Literature 4, a process for obtaining a water-insolubilized film by subjecting carboxymethylcellulose to ion exchange using a metal salt is described.

In Patent Literature 5, a process for insolubilizing sodium hyaluronate in water by cooling a sodium hyaluronate aqueous solution at −20° C. under an acidic condition to form intramolecular crosslinks is described. Moreover, in Patent Literature 6, acetylation of hyaluronic acid performed by reacting a hyaluronic acid in a powder form with acetic anhydride in the presence of concentrated sulfuric acid is described, and further, in Patent Literature 7, a process for producing hyaluronic acid gel using an acidic liquid containing an alcohol is described.

CITATION LIST

Patent Literature

Patent Literature 1: National Publication of International Patent Application No. 2003-518167
Patent Literature 2: Japanese Patent Laid-Open No. 5-124968
Patent Literature 3: Japanese Patent Laid-Open No. 2008-13510
Patent Literature 4: Japanese Patent Laid-Open No. 6-128395
Patent Literature 5: Japanese Patent Laid-Open No. 2003-252905
Patent Literature 6: Japanese Patent Laid-Open No. 8-53501
Patent Literature 7: Japanese Patent Laid-Open No. 5-58881

SUMMARY OF INVENTION

Technical Problem

However, since a crosslinking agent is used in the process described in Patent Literature 1, it is difficult to apply the process in many cases when safety has to be taken into account, such as applications where pharmaceuticals are administered to human bodies. Moreover, the extent of water-insolubility of the obtained films and the like is not described at all in Patent Literatures 2 to 4.

Further, the process described in Patent Literature 5 requires that the pH of the sodium hyaluronate aqueous solution be adjusted so as to be about 1.2, and remarkably increases the viscosity, making it difficult to handle the sodium hyaluronate aqueous solution during molding or the like. Moreover, freeze drying for a long period of time is required, and therefore the process has also a problem in terms of cost of electric power for cooling. Furthermore, when the sodium hyaluronate aqueous solution is placed under an acidic condition, the viscosity rapidly increases to make it difficult to perform molding, and therefore the application is limited in some cases. It is to be noted that, in Patent Literature 5, an intramolecular crosslinked structure is confirmed but the extent of insolubilization is not referred to.

Moreover, in Patent Literature 6, the extent of water-insolubility of the obtained acetylation product of hyaluronic acid is not described at all. Further, the hyaluronic acid gel obtained by the process described in Patent Literature 7 contains a large amount of water, making it difficult to lift the gel. Thus, it is difficult to complete insolubilization while maintaining the shape of a shaped material.

The present invention has been made in consideration of the problems of such conventional technologies, and the subject of the present invention is to provide a process for simply producing a water-insoluble shaped material in which intrinsic characteristics of the polyanionic polysaccharide being a raw material are retained, which has a high safety in that a chemical crosslinking agent is not required, and which is useful as a medical material, a food material, a cosmetic material, and the like. Moreover, the subject of the present invention is to also provide a water-insoluble shaped material produced by the process, an adhesion inhibitor, an injection material, and a sustained release preparation.

Solution to Problem

The present inventors have conducted diligent studies for the purpose of achieving the subjects to find that it is possible to achieve the subjects without using a chemical crosslinking agent by treating a raw material shaped material that is formed using a water-soluble salt of a polyanionic polysaccharide with a treatment liquid containing an acid anhydride, and have completed the present invention.

That is to say, according to the present invention, the following process for producing a water-insoluble shaped material is provided.

[1] A process for producing a water-insoluble shaped material, including a step of treating a raw material shaped material containing a water-soluble salt of a polyanionic polysaccharide with a treatment liquid containing an acid anhydride to insolubilize the raw material shaped material in water.

[2] The process for producing a water-insoluble shaped material according to [1], wherein the raw material shaped material has a shape of a film form, a lump form, a fiber form, a rod form, a tube form, a powder form, a particle form, or a sponge form.

[3] The process for producing a water-insoluble shaped material according to [1] or [2], wherein the polyanionic polysaccharide is at least one selected from the group consisting of carboxyalkylcelluloses, carboxymethylstarches, chondroitin sulfate, hyaluronic acid, heparin, alginic acid, pectin, and carrageenan.

[4] The process for producing a water-insoluble shaped material according to any one of [1] to [3], wherein the acid anhydride is at least one selected from the group consisting of acetic anhydride, propionic anhydride, succinic anhydride, butyric anhydride, phthalic anhydride, and maleic anhydride.

[5] The process for producing a water-insoluble shaped material according to any one of [1] to [4], wherein the treatment liquid further comprises at least any one of media of water and a water-soluble organic solvent.

[6] The process for producing a water-insoluble shaped material according to [5], wherein the water-soluble organic solvent is at least one selected from the group consisting of methanol, ethanol, propanol, dimethyl sulfoxide, acetonitrile, and tetrahydrofuran.

Moreover, according to the present invention, the following water-insoluble shaped material is provided.

[7] A water-insoluble shaped material produced by the production process according to any one of [1] to [6].

[8] A water-insoluble shaped material obtained by eliminating, from a raw material shaped material containing a water-soluble salt of a polyanionic polysaccharide, at least part of cationic species constituting the salt, the water-insoluble shaped material having a swelling ratio of 6,000% by mass or less.

[9] A water-insoluble shaped material containing a polyanionic polysaccharide, wherein a dried body obtained by performing twice an operation of swelling the water-insoluble shaped material with water and then drying the swollen body has a mass being 80% or more of a mass on a dry basis before the operations.

[10] The water-insoluble shaped material according to any one of [7] to [9], dissolving in an aqueous medium having a pH of 12 or more.

[11] The water-insoluble shaped material according to anyone of [7] to [10], being a medical material, a food material, or a cosmetic material.

Further, according to the present invention, the following adhesion inhibitor is provided.

[12] An adhesion inhibitor, wherein a polyhydric alcohol or a polyhydric alcohol aqueous solution is retained in the water-insoluble shaped material according to any one of [7] to [11].

Moreover, according to the present invention, the following injection material is provided.

[13] An injection material containing the water-insoluble shaped material in a powder form or a particle form according to any one of [7] to [11].

[14] The injection material according to [13], further containing an aqueous solution of a water-soluble salt of hyaluronic acid.

[15] The injection material according to [13] or [14], being an intraarticular injection material or subcutaneous injection material for treating arthrosis deformans.

Furthermore, according to the present invention, the following sustained release preparation is provided.

[16] A sustained release preparation containing the water-insoluble shaped material according to any one of [7] to [11] and a pharmaceutically allowable active ingredient.

Advantageous Effects of Invention

The process for producing a water-insoluble shaped material according to the present invention makes it possible to simply produce, without using a chemical crosslinking agent, a water-insoluble shaped material in which intrinsic characteristics of the polyanionic polysaccharide being a raw material are retained, which has a high safety in that a chemical crosslinking agent is not required, and which is useful as a medical material, a food material, a cosmetic material, and the like.

BRIEF DESCRIPTION OF DRAWINGS

FIG. 1 shows an infrared absorption spectrum of a sodium hyaluronate film (before water-insolubilizing treatment) obtained in Example 1.

FIG. 2 shows an infrared absorption spectrum of a water-insoluble film (after water-insolubilizing treatment) obtained in Example 1.

FIG. 3 shows a fluorescent X-ray spectrum of a sodium hyaluronate film (before water-insolubilizing treatment) obtained in Example 1.

FIG. 4 shows a fluorescent X-ray spectrum of a water-insoluble film (after water-insolubilizing treatment) obtained in Example 1.

DESCRIPTION OF EMBODIMENTS

Hereinafter, the embodiments according to the present invention will be described, however the present invention is not limited to the following embodiments.

(Water-Insoluble Shaped Material and Production Process Thereof)

The process for producing a water-insoluble shaped material according to the present invention includes a step (water-insolubilizing step) of forming the water-insoluble shaped material by treating a raw material shaped material containing a water-soluble salt of a polyanionic polysaccharide with a treatment liquid containing an acid anhydride to insolubilize the raw material shaped material in water. Hereinafter, the details of the production process will be described.

The raw material shaped material for use in the water-insolubilizing step is formed using a water-soluble salt of a polyanionic polysaccharide. The polyanionic polysaccharide is a polysaccharide having one or more negatively charged anionic groups such as a carboxy group and a sulfonic acid group in a molecular structure thereof. Moreover, the water-soluble salt of a polyanionic polysaccharide is a compound in which at least part of the anionic groups in the polyanionic polysaccharide forms a salt. In addition, the anionic group in the polyanionic polysaccharide may be an anionic group introduced in the molecule of the polysaccharide.

Specific examples of the polyanionic polysaccharide include carboxyalkylcelluloses such as carboxymethylcellulose and carboxyethylcellulose, carboxymethylstarch, carboxymethylamylose, chondroitin sulfate (including chondroitin-4-sulfate and chondroitin-6-sulfate), hyaluronic acid, heparin, heparin sulfate, heparan sulfate, alginic acid, pectin, carrageenan, dermatan sulfate, and dermatan-6-sulfate. These polyanionic polysaccharides can be used alone or in combination of two or more.

Examples of the water-soluble salt of the polyanionic polysaccharide include inorganic salts, ammonium salts, and organic amine salts. Specific examples of the inorganic salt include: salts of alkali metals such as sodium and potassium; alkali earth metal salts such as calcium salts; and salts of metals such as zinc and iron.

The raw material shaped material can be obtained, for example, in such a way that an aqueous solution obtained by dissolving a water-soluble salt of a polyanionic polysaccharide in water is molded in a desired form, and then drying or the like is conducted. Examples of the shape of the raw material shaped material include a film form, a lump form, a fiber form, a rod form, a tube form, a powder form, a particle form, and a sponge form. The water-insoluble shaped material having a shape such as a film form, a lump form, a fiber form, a rod form, a tube form, a powder form, a particular form, and a sponge form according to the application can be obtained by insolubilizing the raw material shaped material having anyone of these shapes in water. In addition, the obtained water-insoluble shaped material is further molded into a desired shape as necessary.

A raw material shaped material having a film form (sheet form) or a lump form (block form or sponge form) can be obtained by, for example, pouring an aqueous solution of a water-soluble salt of a polyanionic polysaccharide into a suitable container, and thereafter drying or freeze-drying the aqueous solution. Moreover, a raw material shaped material having a fiber form can be obtained by extruding, from a nozzle, an aqueous solution of a water-soluble salt of a polyanionic polysaccharide into a poor solvent. A raw material shaped material having a rod form can be obtained by filling an aqueous solution of a water-soluble salt of a polyanionic polysaccharide in a suitable tube, and thereafter drying and freeze drying the aqueous solution. Furthermore, a raw material shaped material having a powder form or a particle form can be obtained by pulverizing a dried polyanionic polysaccharide into a powder. In this way, the process for producing a water-insoluble shaped material according to the present invention makes it possible to obtain a water-insolubilized product (water-insoluble shaped material) having a shape according to the application because water-insolubilizing treatment is performed after forming the polyanionic polysaccharide into a desired shape.

The treatment liquid used for treating the raw material shaped material contains an acid anhydride. Specific examples of the acid anhydride include acetic anhydride, propionic anhydride, succinic anhydride, butyric anhydride, phthalic anhydride, and maleic anhydride. Among others, acetic anhydride and propionic anhydride are preferable. These acid anhydrides can be used alone or in combination of two or more.

It is preferable that the treatment liquid further contains at least anyone of media of water and a water-soluble organic solvent and an acid anhydride is dissolved or dispersed in the medium. Use of the treatment liquid in which an acid anhydride is dissolved or dispersed in such a medium makes it possible to sufficiently and quickly insolubilize the raw material shaped material to obtain a water-insoluble shaped material.

Specific examples of the water-soluble organic solvent include methanol, ethanol, propanol, dimethyl sulfoxide (DMSO), acetonitrile, and tetrahydrofuran. Among others, methanol, ethanol, and dimethyl sulfoxide are preferable. These water-soluble organic solvents can be used alone or in combination of two or more.

The concentration of the acid anhydride in the treatment liquid is usually 0.1 to 50% by mass, and the concentration of 5 to 30% by mass is preferable. When the concentration of the acid anhydride is less than 0.1% by mass, there is a tendency that the extent of water-insolubility of the water-insoluble shaped material to be obtained is insufficient or water-insolubilization requires a long time. On the other hand, when the concentration of the acid anhydride exceeds 50% by mass, there is a tendency that the effects hit a peak.

In addition, the polyanionic polysaccharide has a high hydrophilicity, and therefore it is preferable that the treatment liquid contains water as a medium from the standpoint of more sufficiently and quickly insolubilizing the raw material shaped material in water. It is preferable that the water content in the treatment liquid is set to an extent that the raw material shaped material does not dissolve or is not swollen. Specifically, it is preferable that the water content in the treatment liquid is 0.01 to 50% by mass, more preferably 5 to 20% by mass. When the water content in the treatment liquid is less than 0.01% by mass, it sometimes occurs that the insolubilization is insufficient in a solvent other than methanol. On the other hand, when the water content in the treatment liquid exceeds 50%, it sometimes occurs that it is difficult to keep the shape of the water-insoluble shaped material to be obtained.

In the water-insolubilizing step, the raw material shaped material is treated with the treatment liquid that contains an acid anhydride. By treating the raw material shaped material with the treatment liquid, the raw material shaped material is insolubilized in water to form a water-insoluble shaped material while the shape of the raw material shaped material is kept. The method for treating the raw material shaped material with the treatment liquid is not particularly limited, however it is preferable to treat the raw material shaped material so that the treatment liquid may make contact with the whole raw material shaped material and the treatment liquid may penetrate into the inside of the raw material shaped material. Specific examples of the treatment method include a method in which the raw material shaped material is immersed in the treatment liquid and a method in which the treatment liquid is applied or blown (sprayed) on the raw material shaped material.

In addition, when the raw material shaped material in a powder form or a particle form is treated to be insolubilized in water, the raw material shaped material in a powder form or a particle form is, in the first place, dispersed in a poor solvent to a water-soluble salt of a polyanionic polysaccharide that constitutes the raw material shaped material. Subsequently, the raw material shaped material may be treated with the treatment liquid by adding the treatment liquid to bring the raw material shaped material in a powder form or a particle form dispersed in the poor solvent and the treatment liquid into contact with each other. As the poor solvent, methanol, ethanol, propanol, dimethyl sulfoxide, acetonitrile, tetrahydrofuran, and the like can be used. These poor solvents can be used alone or in combination of two or more. In addition, the poor solvent may contain a trace amount of water to an extent that the raw material shaped material in a powder form or a particle form does not dissolve.

Moreover, the temperature during treatment is not particularly limited as long as the temperature does not exceed the boiling point of the treatment liquid. It is preferable to set the temperature during treatment to 0 to 80° C. from the standpoint of suppressing the denaturation by decomposition of the polyanionic polysaccharide and from the standpoint of suppressing vaporization of the medium, by-products, and the like, more preferably 0 to 70° C., particularly preferably room temperature (25° C.) to 60° C. However, the water-insoluble shaped material can be obtained in a shorter time without causing the denaturation by decomposition or the like when the treatment is performed under a condition that the treatment liquid is not vaporized during the treatment, for example, with a heat press or a heat roller. For example, when the treatment is performed with a heat press or a heat roller, it is preferable to set the temperature during treatment to 50 to 90° C., and it is preferable to set the treatment time to 30 minutes or shorter. After the water-insolubilizing step, the water-insoluble shaped material according to the present invention can be obtained by washing or the like with water, a water-soluble organic solvent, or the like when necessary.

The reaction that is assumed to occur when the raw material shaped material formed using a sodium salt of a polyanionic polysaccharide is treated with an alcohol solution of acetic anhydride is shown below. In addition, the assumed reaction can be a factor of water-insolubilization, however there is a possibility that water-insolubilization is brought about due to the combination with different factor or factors of water-insolubilization or due to a totally different factor. That is to say, the present invention is not limited at all by the following assumed reaction.

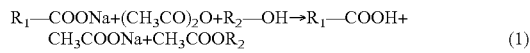

$$R_1\text{—COONa}+(CH_3CO)_2O+R_2\text{—OH} \rightarrow R_1\text{—COOH}+CH_3COONa+CH_3COOR_2 \qquad (1)$$

In the reaction formula (1), $R_1$ represents the main chain of a polyanionic polysaccharide, and $R_2$ represents the main chain of an alcohol. Acetic anhydride, when cleaved in the presence of an alcohol, deprives sodium of the polyanionic polysaccharide to change the carboxy group in the polyanionic polysaccharide into an acid form from a sodium salt form. The change can be confirmed by the measurement of the Na content in the water-insoluble shaped material or the titration of the water-insoluble shaped material with an alkaline solution.

When water is present in the reaction system, it is presumed that, in addition to the reaction represented by the reaction formula (1), the reaction represented by the following formula (2) progresses in parallel and the carboxy group changes into an acid form from a sodium salt form.

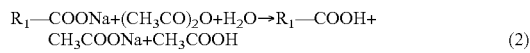

$$R_1\text{—COONa}+(CH_3CO)_2O+H_2O \rightarrow R_1\text{—COOH}+CH_3COONa+CH_3COOH \qquad (2)$$

In addition, all of the anionic groups in the molecule may not be changed into the acid form in the water-insoluble shaped material to be obtained.

It is extremely difficult to obtain a shaped material that is sufficiently insolubilized in water even when the raw material shaped material formed using a water-soluble salt of a polyanionic polysaccharide is immersed in an inorganic acid such as hydrochloric acid or an organic acid such as acetic acid. Moreover, the water-insoluble shaped material cannot be obtained by replacing the acid anhydride in the treatment liquid with the corresponding acid to the acid anhydride. From these facts, it is presumed that the water-insoluble shaped material is obtained due to additional factor or factors other than and together with the factor that the anionic groups in the polyanionic polysaccharide changes into the acid form.

In the process for producing the water-insoluble shaped material according to the present invention, it is not necessary to use a chemical crosslinking agent, and therefore a structure of a functional group or the like derived from the chemical crosslinking agent is not taken in a molecule that constitutes the water-insoluble shaped material to be obtained. Thus, in the water-insoluble shaped material according to the present invention produced by the production process, inherent characteristics of the polyanionic polysaccharide as a raw material are retained, and the water-insoluble shaped material has a high safety. Accordingly, the water-insoluble shaped material according to the present invention is suitable for a food material or cosmetic material as well as a medical material such as an adhesion inhibitor.

In addition, the "water-insolubility" in the present DESCRIPTION means a property that a compound does not easily dissolve in water. More specifically, a dried body obtained by performing twice an operation of swelling the water-insoluble shaped material according to the present invention containing a polyanionic polysaccharide with water and then drying the swollen body has a mass being 80% or more of a mass on a dry basis before the operations.

The water-insoluble shaped material according to the present invention is produced by eliminating, from the raw material shaped material containing a water-soluble salt of a polyanionic polysaccharide, at least part of cationic species constituting the salt. And, it is preferable that the water-insoluble shaped material according to the present invention has a swelling ratio of 6,000% by mass or less, more preferably 900% by mass or less, particularly preferably 100 to 500% by mass, most preferably 150 to 350% by mass. Among the water-insoluble molded bodies according to the present invention, the water-insoluble shaped material having a sufficiently low swelling ratio is suitable for a food material or cosmetic material as well as a medical material such as an adhesion inhibitor. The "swelling ratio" in the present DESCRIPTION means a ratio (% by mass) of the "mass of the water-insoluble shaped material after retaining water (after swelling)" to the "mass of the water-insoluble shaped material before retaining water (before swelling)". In addition, the water-insoluble shaped material having a relatively low swelling ratio (for example, 6,000% by mass or less) can be produced by increasing the amount of water in the treatment liquid within a range that does not exceed, for example, 20% by mass. Moreover, the water-insoluble shaped material having a relatively low swelling ratio (for example, 6,000% by mass or less) can be produced by increasing the amount of the acid anhydride (for example, upper limit is 20% by mass) in the treatment liquid.

The water-insoluble shaped material according to the present invention is obtained without using a chemical crosslinking agent by treating the raw material shaped material containing a water-soluble salt of a polyanionic polysaccharide with the treatment liquid containing an acid anhydride to insolubilize the raw material shaped material in water. Thus, in the water-insoluble shaped material according to the present invention, the molecules of the polyanionic polysaccharide constituting the water-insoluble shaped material are not substantially crosslinked. Further, covalent bonds are not substantially formed anew in the polyanionic polysaccharide. However, it is inferred that physical bonds such as hydrogen bonds, hydrophobic bonds, and Van der Waals bonds are formed between molecules of the polyanionic polysaccharide that constitutes the water-insoluble shaped material according to the present invention. The formation of such physical bonds between molecules of the polyanionic polysaccharide can be confirmed by measuring the infrared absorption spectrum.

The water-insoluble shaped material according to the present invention is stably water-insoluble in a wide pH range from acidic to alkaline regions. However, the water-insoluble shaped material according to the present invention, when made contact with or immersed in an aqueous medium having a pH of, for example, 12 or more, can easily dissolve as a result of dissociation of physical bonds between molecules.

(Adhesion Inhibitor and Production Process Thereof)

Next, the process for producing an adhesion inhibitor according to the present invention will be described. The process for producing an adhesion inhibitor according to the present invention includes a step of retaining a polyhydric alcohol or a polyhydric alcohol aqueous solution in the aforementioned water-insoluble shaped material. Specific examples of the polyhydric alcohol include ethylene glycol, diethylene glycol, polyethylene glycol, methyl glycerol, polyoxyethylene glycosides, maltitol, mannitol, xylitol, sorbitol, reduced sugar syrup, dipropylene glycol, butylene glycol, valine, propylene glycol, glycerin (glycerol), polyglycerin, glycerin fatty acid esters. Among them, polyhydric alcohols used in medical fields and food fields, such as glycerin, xylitol, sorbitol, and low-molecular weight polyethylene glycols, are suitably used. These polyhydric alcohols suitably used are available from the market and can be used as received. It is desirable to use glycerin, sorbitol, and the like that conform to the Japanese Pharmacopoeia. Glycerin is particularly preferable because glycerin is a high-safety material to such an extent that it is also used as an injection agent for a vein.

Examples of the method for retaining the polyhydric alcohol or polyhydric alcohol aqueous solution in the water-insoluble shaped material include a method in which the water-insoluble shaped material is immersed in the polyhydric alcohol or the polyhydric alcohol aqueous solution having a predetermined concentration. That is to say, a desired adhesion inhibitor according to the present invention can be obtained by immersing the water-insoluble shaped material having a predetermined shape in a polyhydric alcohol aqueous solution and replacing the inside of the water-insoluble shaped material with the polyhydric alcohol aqueous solution to retain the polyhydric alcohol aqueous solution with a desired concentration.

(Injection Material)

The injection material according to the present invention contains a water-insoluble shaped material the shape of which is a powder form or a particle form among the aforementioned water-insoluble molded bodies. The injection material according to the present invention may further contain a liquid medium such as an aqueous solution of a water-soluble salt of hyaluronic acid that is not insolubilized in water. As mentioned previously, the water-insoluble shaped material that constitutes the injection material according to the present invention can be produced without using a chemical crosslinking agent, retains the intrinsic characteristics of the polyanionic polysaccharide being a raw material, and therefore is excellent in safety. Moreover, the injection material according to the present invention contains a water-insoluble shaped material in a powder form or a particle form resulting in a high fluidity, and therefore can easily be injected into an affected part through an injection needle by appropriately adjusting the particle diameter of the powder or particle. Thus, the injection material according to the present invention is useful as, for example, an intraarticular injection material and a subcutaneous injection material for treating arthrosis deformans.

(Sustained Release Preparation)

The sustained release preparation according to the present invention contains the aforementioned water-insoluble shaped material and a pharmaceutically allowable active ingredient. As mentioned previously, the water-insoluble shaped material that constitutes the sustained release preparation according to the present invention can be produced without using a chemical crosslinking agent, retains the intrinsic characteristics of the polyanionic polysaccharide being a raw material, and therefore is excellent in safety. Moreover, the active ingredient can be released gradually because the water-insoluble shaped material is gradually decomposed and absorbed in vivo. In addition, the kind of the active ingredient is not particularly limited as long as the active ingredient is pharmaceutically allowable.

Examples of the embodiment of the sustained release preparation include a preparation in which a water-insoluble shaped material molded in a sheet form is impregnated with an active ingredient or a solution of the active ingredient, and a preparation containing: a capsule made of a water-insoluble shaped material; and an active ingredient sealed in the capsule. Sustained release properties in vivo can be controlled by appropriately setting the thickness, the shape, or the like of the sheet or capsule.

EXAMPLES

Hereinafter, the present invention will be descried specifically based on Examples, however the present invention is not limited to these Examples. In addition, "%" in Examples and Comparative Examples is based on mass unless otherwise noted.

Example 1

1.0 g of sodium hyaluronate (molecular weight (nominal value): 800000, manufactured by Kikkoman Biochemifa Company) and 99.0 g of water were mixed and stirred in a beaker to obtain a uniform aqueous solution. The obtained aqueous solution was poured into a stainless steel vat and dried at 30° C. to obtain a sodium hyaluronate film. The obtained sodium hyaluronate film was immersed in 100 mL of a treatment liquid (1% by volume acetic anhydride methanol solution) and left at room temperature for 18 hours to apply water-insolubilizing treatment. The film to which the water-insolubilizing treatment was applied was washed with methanol, an 80% by volume methanol aqueous solution, and water in this order to obtain a water-insoluble film.

FIG. 1 shows an infrared absorption spectrum of the sodium hyaluronate film (before water-insolubilizing treatment) obtained in Example 1. And, FIG. 2 shows an infrared absorption spectrum of the water-insoluble film (after water-insolubilizing treatment) obtained in Example 1. As shown in FIGS. 1 and 2, it is understand that, due to the water-insolubilizing treatment, the absorption at 1400 $cm^{-1}$ (Arrow 1 (FIG. 1)) and the absorption at 1600 $cm^{-1}$ (Arrow 2 (FIG. 1)) both originated from dissociated carboxy groups were decreased, and the absorption at 1220 $cm^{-1}$ (Arrow 3 (FIG. 2)) and the absorption at 1730 $cm^{-1}$ (Arrow 4 (FIG. 2)) were increased.

FIG. 3 shows a fluorescent X-ray spectrum of the sodium hyaluronate film (before water-insolubilizing treatment)

obtained in Example 1. And, FIG. 4 shows a fluorescent X-ray spectrum of the water-insoluble film (after water-insolubilizing treatment) obtained in Example 1. By comparing these figures (spectra), the change of the amount of sodium in the film caused by the water-insolubilizing treatment is determined. That is to say, as shown in FIGS. 3 and 4, it is understood that the amount of sodium in the film was decreased to about ¼ by the water-insolubilizing treatment.

Moreover, $^{13}$C-NMR analysis was performed to the sodium hyaluronate film (before water-insolubilizing treatment) and water-insoluble film (after water-insolubilizing treatment) obtained in Example 1. As a result thereof, an O-acetyl group and an ester bond formed between a carboxy group and a hydroxy group were not observed even after the water-insolubilizing treatment. From the above results, it is presumed that the reactions represented by the reaction formulas (1) and (2) occurred due to the water-insolubilizing treatment and several factors including these reactions contribute to the water-insolubilization of sodium hyaluronate film.

Examples 2 to 13 and Comparative Examples 1 to 3

Water-insoluble films were obtained in the same manner as in Example 1 except that the water-soluble salts of polyanionic polysaccharides and treatment liquids shown in Table 1 were used.

(Evaluation 1: Solubility Test)

Each of the water-insoluble films cut in a square the side of which was 2 cm was placed in a container having a diameter of 3.5 cm and a depth of 1.5 cm, and 5 ml of a PBS buffer solution (pH of 6.8) was added thereto. The container was placed in a shaker the temperature of which was adjusted to 37° C. and shaken at 10 to 20 rpm. The change in the state of each water-insoluble film with time was visually observed to evaluate the water-insolubility of each film in accordance with the evaluation criteria shown below. The results are shown in Table 2.

Excellent: the film was insolubilized in water, and the original shape was kept.

Good: the film was insolubilized in water, but was fragmented.

Fair: the film became water-insoluble gel, and the original shape was not kept.

Poor: the film was not insolubilized in water, and dissolved.

(Evaluation 2: Measurement of Swelling Ratio)

The swelling ratio of each prepared water-insoluble film was measured by the following procedure. The mass of the water-insoluble film in a dried state was measured and defined as the "mass before swelling". Subsequently, the water-insoluble film was immersed in a sufficient amount of water and left at room temperature for 1 hour. The excessive water adhered to the surface of the sufficiently-swollen water-insoluble film was removed with a paper towel or the like, and the mass was measured and defined as the "mass after swelling". The "swelling ratio" means a ratio (% by mass) of the "mass after swelling" to the "mass before swelling". The results are shown in Table 2. In addition, it was difficult to hold up the water-insoluble film produced in Example 1 from water for immersion and remove excessive water adhered to the surface thereof, and therefore the swelling ratio was not able to be measured.

(Evaluation 3: Measurement of Non-Dissolution Ratio)

Each prepared water-insoluble film was immersed in a sufficient amount of water (25° C.) for 1 hour to be swollen, and thereafter dried under ventilation of a clean bench or the like. Swelling/drying treatment performing swelling and drying twice was applied, and thereafter the mass of the obtained dried body was measured. And the non-dissolution ratio was calculated in accordance with the following formula. The results are shown in Table 2. In addition, it was difficult to hold up the water-insoluble film produced in Example 1 from water for immersion, and therefore the non-dissolution ratio was not able to be measured.

Non-dissolution ratio (%)=(Y/X)×100 wherein X: mass (g) of dried body of water-insoluble film before swelling/drying treatment (initial), and
Y: mass (g) of dried body of water-insoluble film after swelling/drying treatment

TABLE 1

| | Water soluble salt of polyanionic polysaccharide | Treatment liquid | | |
|---|---|---|---|---|
| | | Acid anhydride | | |
| | | Kind | Conc. (%) | Solvent |
| Example 1 | Sodium hyaluronate | Acetic anhydride | 1 | Methanol |
| Example 2 | Sodium hyaluronate | Acetic anhydride | 2 | Methanol |
| Example 3 | Sodium hyaluronate | Acetic anhydride | 3 | Methanol |
| Example 4 | Sodium hyaluronate | Acetic anhydride | 5 | Methanol |
| Example 5 | Sodium hyaluronate | Acetic anhydride | 10 | Methanol |
| Example 6 | Sodium hyaluronate | Acetic anhydride | 20 | Methanol |
| Comparative Example 1 | Sodium hyaluronate | — | — | Methanol |
| Comparative Example 2 | Sodium hyaluronate | — | — | 1N Hydrochloric acid in methanol |
| Comparative Example 3 | Sodium hyaluronate | — | — | 10% Acetic acid in methanol |
| Example 7 | Sodium hyaluronate | Propionic anhydride | 10 | Methanol |
| Example 8 | Sodium hyaluronate | Acetic anhydride | 10 | 90% Methanol aqueous solution |
| Example 9 | Sodium hyaluronate | Acetic anhydride | 10 | 80% Ethanol aqueous solution |
| Example 10 | Sodium carboxymethylcellulose | Acetic anhydride | 10 | Methanol |
| Example 11 | Sodium alginate | Acetic anhydride | 10 | Methanol |
| Example 12 | Sodium hyaluronate | Acetic anhydride | 10 | 80% DMSO aqueous solution |
| Example 13 | Ammonium carboxymethylcellulose | Acetic anhydride | 10 | 80% Ethanol aqueous solution |

TABLE 2

| | Solubility test | | | Swelling ratio (%) | Non-dissolution ratio (%) |
|---|---|---|---|---|---|
| | 1 hour | 24 hours | 72 hours | | |
| Example 1 | Good | Good | Good | — | — |
| Example 2 | Excellent | Good | Good | 4,140 | 81 |
| Example 3 | Excellent | Good | Good | 3,600 | 94 |
| Example 4 | Excellent | Excellent | Excellent | 5,800 | 93 |
| Example 5 | Excellent | Excellent | Excellent | 3,100 | 96 |
| Example 6 | Excellent | Excellent | Excellent | 3,300 | 97 |
| Comparative Example 1 | Poor | — | — | — | — |
| Comparative Example 2 | —* | — | — | — | — |
| Comparative Example 3 | Poor | — | — | — | — |
| Example 7 | Excellent | Excellent | Excellent | 420 | 98 |
| Example 8 | Excellent | Excellent | Excellent | 320 | 98 |
| Example 9 | Excellent | Excellent | Excellent | 260 | 98 |
| Example 10 | Excellent | Excellent | Excellent | 370 | 97 |
| Example 11 | Excellent | Excellent | Excellent | 360 | 98 |
| Example 12 | Excellent | Excellent | Excellent | 340 | 98 |
| Example 13 | Excellent | Excellent | Excellent | 360 | 98 |

*Water-insoluble film was not able to be produced.

Comparative Example 4

1.0 g of sodium hyaluronate (molecular weight (nominal value): 800000, manufactured by Kikkoman Biochemifa Company) and 99.0 g of water were mixed and stirred in a beaker to make the resultant mixture uniform, and thereafter 1N hydrochloric acid was added to prepare an aqueous solution having a pH of 2.5. The obtained aqueous solution was poured into a stainless steel vat and dried at 30° C. to form a film. The aforementioned "Solubility Test" was performed to the formed film to find that the film absorbed water to be swollen into a lump form, and the original form was not kept. Moreover, the film that was swollen into a lump form gradually dissolved to become small.

Example 14

1.0 g of sodium hyaluronate (molecular weight (nominal value): 800000, manufactured by Kikkoman Biochemifa Company) and 99.0 g of water were mixed and stirred in a beaker to obtain a uniform aqueous solution. The obtained aqueous solution was poured into a stainless steel vat and dried at 30° C. to obtain a sodium hyaluronate film. The obtained sodium hyaluronate film was immersed in 100 mL of a treatment liquid (100% acetic anhydride) and left at room temperature for 18 hours, however the obtained sodium hyaluronate film was not sufficiently insolubilized in water. On the other hand, the obtained sodium hyaluronate film was immersed in 100 mL of a treatment liquid (100% acetic anhydride) and left at room temperature for 10 days to apply water-insolubilizing treatment. The film to which the water-insolubilizing treatment was applied was washed with methanol, an 80% by volume methanol aqueous solution, and water in this order to obtain a water-insoluble film. The aforementioned "Solubility Test" was performed to the obtained water-insoluble film to find that the original shape of the film was kept for 72 hours or longer.

Example 15

1.0 g of sodium hyaluronate (molecular weight (nominal value): 800000, manufactured by Kikkoman Biochemifa Company) and 99.0 g of water were mixed and stirred in a beaker to obtain a uniform aqueous solution. The obtained aqueous solution was poured into a stainless steel vat, frozen at −30° C., and freeze-dried at a shelf heating temperature of 120° C. to obtain a shaped material in a sponge form made of sodium hyaluronate. The obtained shaped material in a sponge form was immersed in 100 mL of a treatment liquid (10% acetic anhydride methanol solution) and left at room temperature for 18 hours to apply water-insolubilizing treatment. The shaped material to which water-insolubilizing treatment was applied was washed with methanol, an 80% by volume methanol aqueous solution, and water in this order to obtain a water-insoluble shaped material in a sponge form. The aforementioned "Solubility Test" was performed to the obtained water-insoluble shaped material in a sponge form to find that the original shape of the sponge form was kept for 72 hours or longer.

Example 16

10 g of sodium hyaluronate (molecular weight (nominal value): 800000, manufactured by Kikkoman Biochemifa Company) was dissolved in 90 g of water to obtain a sodium hyaluronate aqueous solution which was uniform and viscous. The obtained sodium hyaluronate aqueous solution was poured into a syringe with an 18 gauge needle attached, and was extruded to obtain a shaped material in a fiber form. The obtained shaped material in a fiber form had a high viscosity, and therefore was kept in a fiber form. The obtained shaped material in a fiber form was immersed in 100 mL of a treatment liquid (10% acetic anhydride methanol solution) and left at room temperature for 18 hours to apply water-insolubilizing treatment. The shaped material to which water-insolubilizing treatment was applied was washed with methanol, an 80% by volume methanol aqueous solution, and water in this order to obtain a water-insoluble shaped material in a fiber form. The aforementioned "Solubility Test" was performed to the obtained water-insoluble shaped material in a fiber form to find that the original shape of the fiber form was kept for 72 hours or longer.

Example 17

The shaped material in a sponge form produced in Example 15 was cut in a cocoon shape, and thereafter was impregnated with a commercially available face lotion. The cocoon-shaped shaped material in a sponge form did not dissolve in the face lotion. Moreover, the cocoon-shaped shaped material in a sponge form had a high sticking performance to skin, and therefore was able to be used as a cosmetic material for sticking to skin around eyes.

Example 18

The water-insoluble film produced in Example 5 and cut in a size of 12 cm×9 cm was immersed in a 10% by volume glycerin aqueous solution, then air-dried, and sealed in a bag for sterilization. The bag for sterilization was irradiated with 25 kGy irradiation rays for sterilization of the water-insoluble film together with the bag to obtain an adhesion inhibition film. A surgical incision was made in the abdomen of a mature dog (beagle dog, female, 1.5 years old, and body weight of 10 kg) after general anesthesia treatment, and the epidermis of the ventral wall was peeled in a square the side of which was 3 cm. The adhesion inhibition film was arranged so as to cover the peeled portion, and then the abdomen was closed. Two weeks later, when surgical incision was made in the abdomen of the same dog after general anesthesia treatment, adhesion was not observed. Moreover, the adhesion inhibition film arranged (implanted) in the body of the dog had disappeared in two weeks after implantation. It is inferred that the reason is because the carboxy groups of hyaluronic acid constituting the adhesion inhibition film were gradually neutralized by sodium ions or the like in vivo and the hyaluronic acid changed into soluble a hyaluronic acid salt, dissolved, and absorbed in vivo. On the other hand, it was observed that adhesion occurred between the peeled portion and the intestine with regard to the dog whose abdomen was closed without arranging the adhesion inhibition film.

Examples 19 to 21

1.0 g of sodium hyaluronate (molecular weight (nominal value): 800000, manufactured by Kikkoman Biochemifa Company) and 99.0 g of water were mixed and stirred in a beaker to obtain a uniform aqueous solution. The obtained aqueous solution was poured into a stainless steel vat and dried at 30° C. to obtain a sodium hyaluronate film. The obtained sodium hyaluronate film was immersed in 100 mL of a treatment liquid (20% acetic anhydride methanol solution) and left at room temperature (25° C.) for 18 hours (Example 19), at 50° C. for 1 hour (Example 20), and at 85° C. for 5 minutes (Example 21) to apply water-insolubilizing treatment. The films to which the water-insolubilizing treatment was applied were washed with methanol, an 80% by volume methanol aqueous solution, and water in this order to obtain water-insoluble films. The aforementioned "Evaluation 1: Solubility Test" was performed to the obtained water-insoluble films to evaluate the water-insolubility. As a result thereof, it was confirmed that all of the films were insolubilized in water and the original shapes of the films were kept for 72 hours or longer. Moreover, the obtained films had a swelling rate of 244% (Example 19), 192% (Example 20), and 161% (Example 21), respectively.

(Evaluation 4: Solubility)

1 g of the water-insoluble film produced in Example 5 was immersed in 10% by volume sodium carbonate aqueous solution to find that the water-insolubilized film dissolved after 30 minutes. On the other hand, 1 g of the water-insoluble film produced in Example 5 was immersed in water to find that the water-insoluble film did not dissolve and the original shape was kept even after 30 minutes elapsed. From the above results, it was confirmed that, in the water-insoluble film according to the present embodiment, carboxy groups of hyaluronic acid were neutralized in the presence of a sodium salt (sodium ion) and the hyaluronic acid changed into a soluble hyaluronic acid salt to gradually dissolve.

(Evaluation 5: Decomposition Property)

1 g of the water-insoluble film produced in Example 5 was immersed in a 5000 units/ml hyaluronidase aqueous solution, and the resultant mixture was placed in a shaker the temperature of which was adjusted to 37° C. and shaken at 10 to 20 rpm. On the other hand, a control test was performed in which 1.0 g of the water-insoluble film produced in Example 5 was immersed in a PBS buffer solution (pH of 6.8), and the resultant mixture was placed in a shaker the temperature of which was adjusted to 37° C. and shaken at 10 to 20 rpm. Five days later, the original shape of the water-insoluble film that had been immersed in the PBS buffer solution was kept, however the water-insoluble film that had been immersed in the hyaluronidase aqueous solution had dissolved completely. It can be said that the water-insoluble film according to the present embodiment had a hyaluronic acid structure resulting in decomposition by the hyaluronidase. From the above results, it is inferred that the water-insoluble film according to the present embodiment, even when arranged in vivo, is metabolized through a metabolic pathway similar to that of water-soluble hyaluronic acid.

(Evaluation 6: Long Term Solubility Test)

The water-insoluble film produced in Example 5 was cut in a square the side of which was 2 cm and placed in a container having a diameter of 3.5 cm and a depth of 1.5 cm, and 5 ml of a PBS buffer solution (pH of 6.8) was added thereto. The container was placed in a shaker the temperature of which was adjusted to 37° C. and shaken at 10 to 20 rpm. As a result thereof, it was revealed that the original shape of the film was kept even after 3 months or more elapsed.

Example 22

1.0 g of sodium hyaluronate powder (molecular weight (nominal value): 800000, manufactured by Kikkoman Biochemifa Company) was added to 64.0 mL of ethanol and stirred in a beaker to obtain a dispersion liquid. Subsequently, 16.0 mL of water was added to the dispersion liquid and further stirred. After 20 mL of acetic anhydride was added thereto, stirring was continued for 18 hours to apply water-insolubilizing treatment. The powder to which the water-insolubilizing treatment was applied was washed with methanol, an 80% by volume methanol aqueous solution, and water in this order to obtain a water-insoluble powder (water-insoluble hyaluronic acid powder). The aforementioned "Evaluation 1: Solubility Test" was performed to the obtained water-insoluble powder to evaluate the water-insolubility. As a result thereof, it was confirmed that the mass of the powder was kept for 72 hours or longer. Moreover, the obtained water-insoluble powder was used for the same animal experiment as in Example 18. As a result thereof, it was confirmed that the water-insoluble powder exhibited an adhesion inhibition effect.

INDUSTRIAL APPLICABILITY

The water-insoluble shaped material according to the present invention is useful as a medical material, a food material, a cosmetic material, and the like.

The invention claimed is:

1. A process for producing a water-insoluble shaped material,
comprising a step of treating a raw material shaped material comprising a water-soluble salt of a polyanionic polysaccharide, with a treatment liquid comprising an acid anhydride so as to insolubilize the raw material shaped material in water and form the water-insoluble shaped material,
wherein the treating step converts the water-soluble salt of the polyanionic polysaccharide to the polyanionic polysaccharide in an acid form,
the water-insoluble shaped material comprises the polyanionic polysaccharide in the acid form, and
the acid anhydride does not form a covalent bond with the polyanionic polysaccharide in the acid form.

2. The process for producing a water-insoluble shaped material according to claim 1, wherein the raw material shaped material is in a shape of a film form, a lump form, a fiber form, a rod form, a tube form, a powder form, a particle form, or a sponge form.

3. The process for producing a water-insoluble shaped material according to claim 1,
wherein the polyanionic polysaccharide is at least one material selected from the group consisting of carboxyalkylcelluloses, carboxymethyl starches, chondroitin sulfate, hyaluronic acid, heparin, alginic acid, pectin, and carrageenan.

4. The process for producing a water-insoluble shaped material according to claim 1,
wherein the acid anhydride is at least one material selected from the group consisting of acetic anhydride, propionic anhydride, succinic anhydride, butyric anhydride, phthalic anhydride, and maleic anhydride.

5. The process for producing a water-insoluble shaped material according to claim 1,
wherein the treatment liquid further comprises at least one liquid selected from the group consisting of media of water and a water-soluble organic solvent.

6. The process for producing a water-insoluble shaped material according to claim 5,
wherein the water-soluble organic solvent is at least one material selected from the group consisting of methanol, ethanol, propanol, dimethyl sulfoxide, acetonitrile, and tetrahydrofuran.

7. The process for producing a water-insoluble shaped material according to claim 1,
wherein the raw material shaped material is insolubilized while maintaining a shape of the raw material shaped material subjected to the treating step.

* * * * *